United States Patent [19]

Wertz et al.

[11] Patent Number: 5,132,791
[45] Date of Patent: Jul. 21, 1992

[54] OPTICAL SHEET INSPECTION SYSTEM

[75] Inventors: Ronald D. Wertz, Boulder; H. Kent Minet, Littleton; Daniel J. Messerschmidt, Broomfield; Carey Brown, Denver, all of Colo.

[73] Assignee: Ball Corporation, Muncie, Ind.

[21] Appl. No.: 587,870

[22] Filed: Sep. 25, 1990

[51] Int. Cl.⁵ .............................................. H04N 7/18
[52] U.S. Cl. ...................................... 358/106; 358/101; 358/107; 356/237; 356/239; 250/572; 250/571; 382/8
[58] Field of Search ............... 358/106, 101, 107; 356/231, 239; 250/572, 571; 382/8

[56] References Cited

U.S. PATENT DOCUMENTS

| | | | |
|---|---|---|---|
| 3,794,427 | 2/1974 | Shibata et al. | 356/237 |
| 4,223,346 | 9/1980 | Neiheisel et al. | 250/572 |
| 4,399,554 | 8/1983 | Pekins, III et al. | 382/8 |
| 4,539,587 | 9/1985 | Eby et al. | 358/106 |
| 4,555,727 | 11/1985 | Nun et al. | 358/106 |
| 4,578,810 | 3/1986 | MacFarlane et al. | 382/8 |
| 4,724,481 | 2/1988 | Nishioka | 356/237 |
| 4,811,410 | 3/1989 | Amin et al. | 382/8 |
| 4,943,734 | 7/1990 | Johnson et al. | 250/572 |
| 4,950,911 | 8/1990 | Williams et al. | 356/237 |
| 4,972,494 | 11/1990 | White et al. | 358/106 |
| 4,974,077 | 11/1990 | Kusaba | 358/107 |
| 4,975,971 | 12/1990 | Ohnishi | 356/237 |
| 5,068,799 | 1/1991 | Jarrett, Jr. | 356/239 |

Primary Examiner—James J. Groody
Assistant Examiner—Michael H. Lee
Attorney, Agent, or Firm—Dorr, Carson, Sloan & Peterson

[57] ABSTRACT

An optical inspection system inspects individual sheets having scrolled and unscrolled edges for defects in a production line with high transfer velocities. Each of the individual sheets are delivered in a production line with some spacing between them and potentially with some degree of skewness and offset from the production center line. The inspection system of the present invention utilizes a formed viewing window over which individual sheets from the production line are delivered. As each sheet is delivered over the formed viewing window, the undersurface of each individual sheet is uniformly and continuously illuminated along the length of the formed viewing window with high intensity diffused light. The reflected light from the surface of each moving individual sheet is captured by at least one video camera. As the sheet moves across the formed viewing window, a line-by-line video image is captured and stored according to a rectangularization technique which eliminates the need for customized masks. An analyzer receives the stored information and analyzes the stored information for the presence of defects.

14 Claims, 8 Drawing Sheets

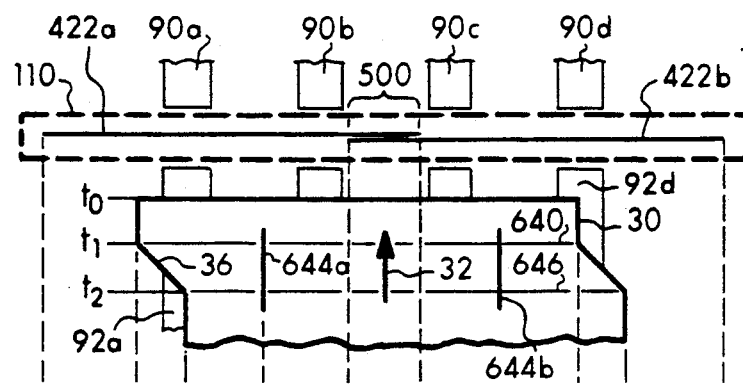
Fig. 6a
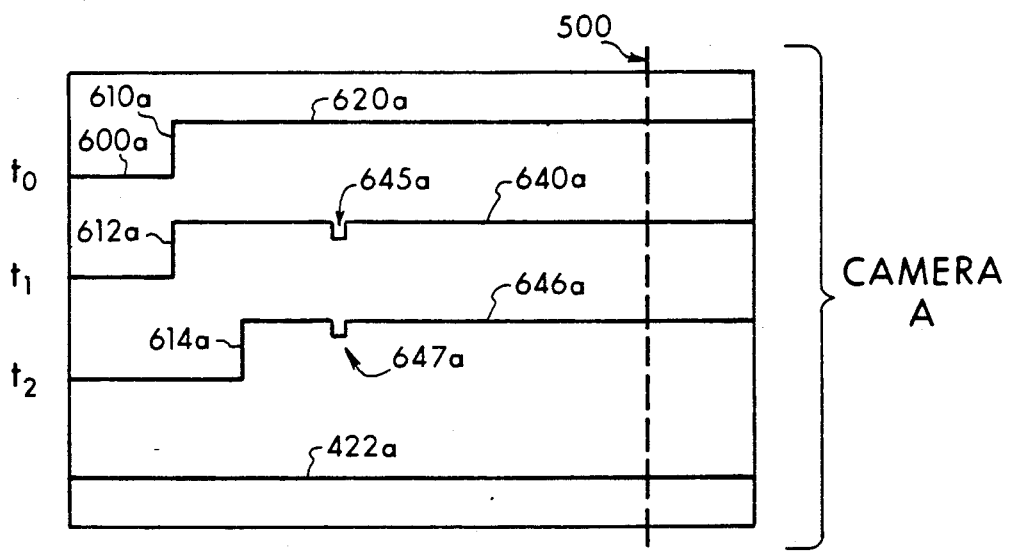
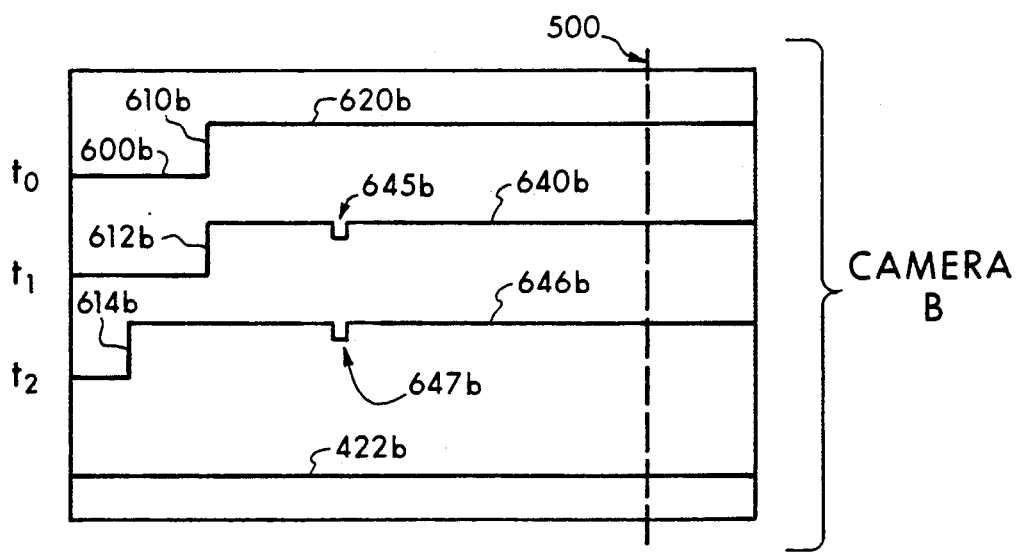
Fig. 6b

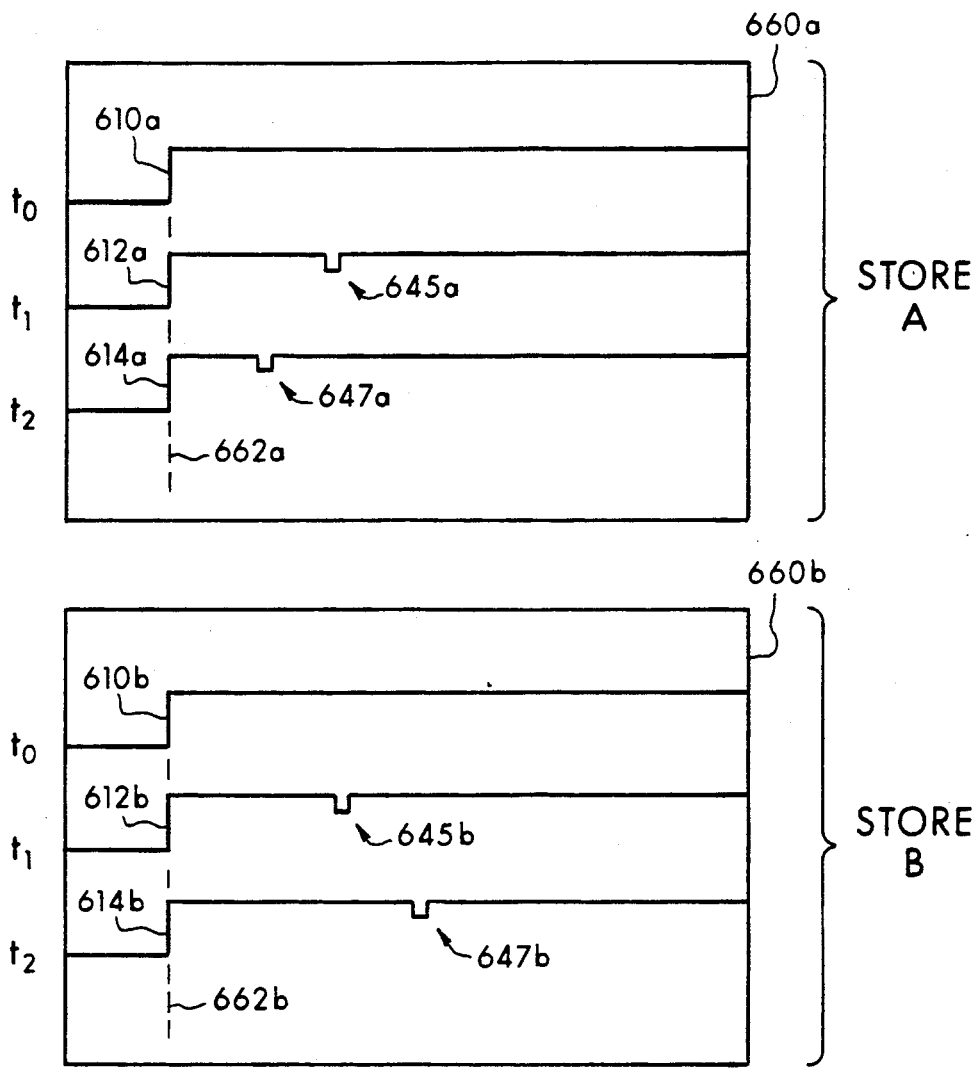
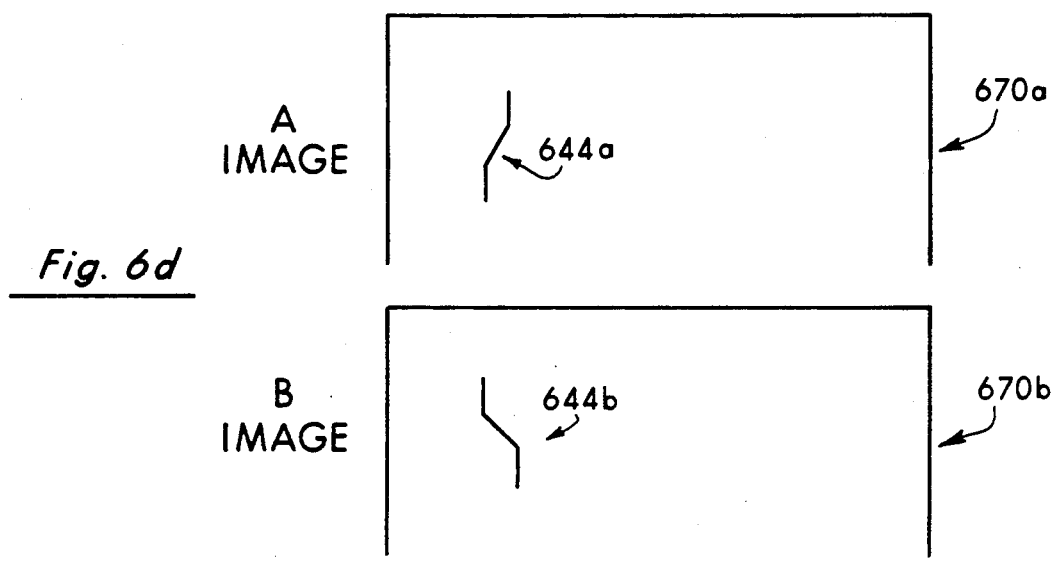
Fig. 6c
Fig. 6d

OPTICAL SHEET INSPECTION SYSTEM

BACKGROUND OF THE PRESENT INVENTION

1. Technical Field

The present invention relates to a system for optically inspecting the surface of moving sheets of material. More particularly, the present invention relates to a system for optically inspecting high velocity individual sheets spaced from each other and having scrolled or unscrolled edges in a production line.

2. Statement of the Problem

In the manufacture of metal containers (such as steel beverage containers), the containers and container ends are stamped from metal sheets. These sheets may be coated, printed upon, or otherwise treated in accordance with the specifications for the desired container. In a sheet coating and decorating production line, the sheets move at high velocities such as 500 feet per minute. At such high velocities, it is impractical to have a person visually scan each sheet to ascertain the presence of defects.

A need, therefore, exists for an automatic optical inspection system and method for optically inspecting the surface of each sheet, at production line velocities, and to reject sheets with unacceptably sized defects from the production line without interfering with the delivery of sheets in the production line.

Since these sheets may have either scrolled or unscrolled edges depending upon the desired specifications, a need further exists for a system and a method which performs automatic optical inspection of each individual sheet whether or not the sheet has scrolled edges. A need further exists for a system and a method to optically inspect the total surface of the sheet including the scrolled edges.

A need also exists for a system and method which performs the optical inspection of the sheets regardless of the spacings between the individual sheets and regardless of the velocity that the sheets are moving in the production line.

Finally, a need exists to provide for the optical inspection of sheets that may be skewed and otherwise misaligned within predetermined amounts as the sheets travel through the production line.

RESULTS OF PATENTABILITY SEARCH

A patentability search was conducted on the present invention. The results of this search are:
Wihl, U.S. Pat. No. 4,633,504, Dec. 30, 1986
Adomaitis et al, U.S. Pat. No. 4,675,730, Jun. 23, 1987
Pietzsch et al., U.S. Pat. No. 4,692,943, Sep. 8, 1987
Lapidot, U.S. Pat. No. 4,758,888, Jul. 19, 1988
Forgues et al., U.S. Pat. No. 4,794,647, Dec. 27, 1988
Huynh et al., U.S. Pat. No. 4,878,114, Oct. 31, 1989
In addition, the inventors are aware of the following commercially available products:
1. Intec Corporation, 1 Trefoil Drive, Trumbull, Conn. 806611—VIGILANT 100 and Series 8000; and
2. Futec Inc., 1217 Hayashi-Cho, Takamatsu, 761-03, Japan—Flawtech—Model PKD and Printec—Model PCB.

In U.S. Pat. No. 4,724,481 assigned to Futec, a flaw detector for detecting flaws in a sheet is disclosed. The flaw detector uses a plurality of linear array cameras which record the images of the sheet as rays of light are transmitted through it. The resultant video signals from the linear array cameras are then processed to ascertain the existence of a flaw. The '481 patent specifically sets forth use of circuitry for correcting sensitivity differences among the cameras and automatic gain controls. The '481 patent detects "transparent flaws" such as a hole in a sheet. It also detects "opaque flaws" such as a black spot on a sheet. This patent is designed principally to detect flaws in sheets of paper, sheet metal, or vinyl film. To eliminate the edge of the sheet problem (appearing as a hole) the '481 patent places an opaque mask on the inner sides of the edges of the sheet. This system is designed for continuous flow of material. For example, in the Futec literature, the FLAWTECH Model PKD is designed for the continuous on-line inspection of plastic film, paper, non-woven cloth, metal foil and plastic. In the PRINTEC, Model PCD, Futec utilizes a CCD linear array sensor which utilizes a camera unit to receive reflected light from a light source. Printed images on the sheet are compared to a running printed pattern for flaws such as pin holes, missing color, black spots, contamination, etc. The PRINTEC system is capable of a maximum line speed of 200 meters per minute (approximately 656 ft./min.) with a minimum flaw size being detected as 0.5 millimeters (approximately 0.127 inches). Again, this system is designed for the evaluation of flaws on a continuous roll of material. Flaw information is generated as to the location of the flaw in the material.

The Intec literature discloses an approach similar to Futec for the detection of defects in continuously moving sheets of material. Intec also utilizes a light source for generating light onto the surface of the continuously moving material for reflection into a camera. The VIGILANT 100 detects defects smaller than one millimeter (i.e., 0.04 inches) in a one meter wide web. The VIGILANT 100 has the capability of automatically adjusting to the edges of the web with no manual adjustments. Since sensitivity may vary across the width of the web, the VIGILANT 100 utilizes a specially designed baseline following electronics technology to compensate for the lack of uniformity. The Futec and Intec approaches do not handle individual sheets in a production line having spaces between each sheet. Nor do these approaches disclose a system for handling and inspecting individual sheets with scrolled or irregular shaped edges. The problem of skewness of the individual sheets is also not addressed by Futec or Intec.

U.S. Pat. No. 4,878,114 sets forth an apparatus for illuminating the surface of material to be inspected and for evaluating the reflected light to provide a parameter indicative of the roughness of the surface.

U.S. Pat. No. 4,794,647 sets forth an automatic optical inspection system for inspecting printed circuit boards. A CCD camera is used to scan the board and to produce a binary image of the board. The electronic image is then processed with dimensional verification and pattern recognition techniques. A light source generates light onto the board which is then reflected into the camera for analysis. Under the teachings of the '647 patent, the camera views a strip on the board one inch wide and 2,048 pixels long.

U.S. Pat. No. 4,758,888 sets forth a system for the inspection of work pieces traveling along a production line. This system detects flaws in the work pieces without interrupting the progression of work pieces along the production line. Down stream, the image optically obtained is reproduced in a monitor for visual inspection whereby an operator can reject the particular piece.

U.S. Pat. No. 4,692,943 sets forth a method and system for the Opto-Electronic inspection of a two-dimensional pattern on an object such as a printed circuit board.

U.S. Pat. No. 4,675,730 sets forth a video surface inspection system for inspecting the surface of a moving object for defects by means of illuminating the surface with both specular and/or diffused light of selected wavelengths. Cameras are used to record images and images are processed for the presence of defects. This system is designed to detect defects in a continuously moving sheet of aluminum material. The material is capable of moving at rates up to 3600 feet per minute.

U.S. Pat. No. 4,633,504, sets forth an automatic photo mask inspection system having image enhancement. This system permits a pixel-by-pixel inspection.

None of the above approaches set forth a solution to the specific needs discussed above present in the optical inspection of individual sheets moving at high velocities in a production line.

SOLUTION TO THE PROBLEM

The present invention provides a solution to the above problem and offers a number of advantages over the background approaches discussed above. The present invention is capable of automatically inspecting individual sheets of material in a high velocity production line by generating a high resolution video image of the surface of each sheet, analyzing the image for defects and then removing those sheets having unacceptable sized defects from the production line.

The forward edge of each individual sheet is detected and, according to a novel circuit arrangement of the present invention, the point of detection is physically spaced from the video cameras so that the cameras are activated to capture the first line of the video image precisely at the leading edge of the sheet.

Under the teachings of the present invention, a pixel-by-pixel image of the entire sheet is obtained which requires high intensity illumination of the area being recorded by the cameras. A novel source of illumination uniformly directs intense diffused light across the width of each individual sheet in a formed viewing window.

In addition, the side edges of the sheet whether scrolled, unscrolled, or any other configuration, are optically analyzed through a unique storing technique for the captured video image in a rectangular format in digital memory thereby allowing inspection of the side edges without the use of a mask.

Also, under the teachings of the present invention, the optical inspection system and method operates independent of individual sheet velocity, sheet spacing and can visually inspect and analyze misaligned or skewed sheets within a certain degree of skewness.

DESCRIPTION OF THE DRAWING

FIG. 6a-d is an illustration setting forth the scan step, line capture step, storage step, and analysis step of the present invention;

SUMMARY OF THE INVENTION

Figure 1:
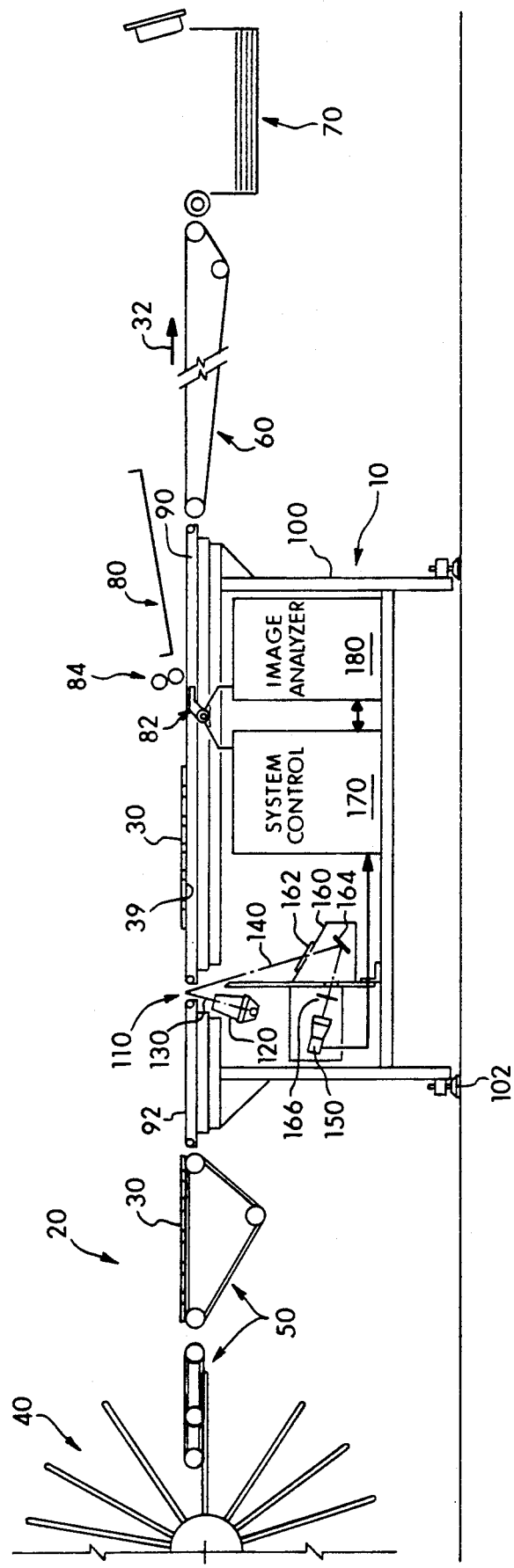
FIG. 1 is an illustration showing the side view of a production line carrying individual sheets over the optical sheet inspection system of the present invention.

The present invention is capable of optically inspecting individual sheets for defects having scrolled and unscrolled edges in a high velocity production line. Each of the individual sheets are delivered in a production line in spaced locations from each other.

The inspection system of the present invention utilizes a formed viewing window having a length perpendicular to the direction of movement of each sheet and having a length greater than the width of each individual sheet. The optical inspection system of the present invention receives individual sheets from the production line and delivers each of the sheets over the formed viewing window.

As each sheet is delivered over the formed viewing window, the undersurface of each individual sheet is uniformly and continuously illuminated along the length of the formed viewing window with high intensity diffused light.

The reflected high intensity diffused light from the surface of each moving individual sheet is captured by at least one video camera. The camera captures video image lines wherein the line is one pixel wide and a sufficient number of pixels in length to equal the width of the individual sheet. As the sheet moves across the formed viewing window, a line-by-line video image is captured and stored.

The present invention stores each line of the video image according to a rectangularization technique which eliminates the need for customized masks.

An analyzer receives the stored information and analyzes the stored information for the presence of defects. If a defect is found, a reject signal is issued and the sheet is rejected and removed from the production line.

The present invention operates at sheet velocities in a range up to 500 feet per minute.

DESCRIPTION OF THE DRAWING

General Overview

Figure 2:
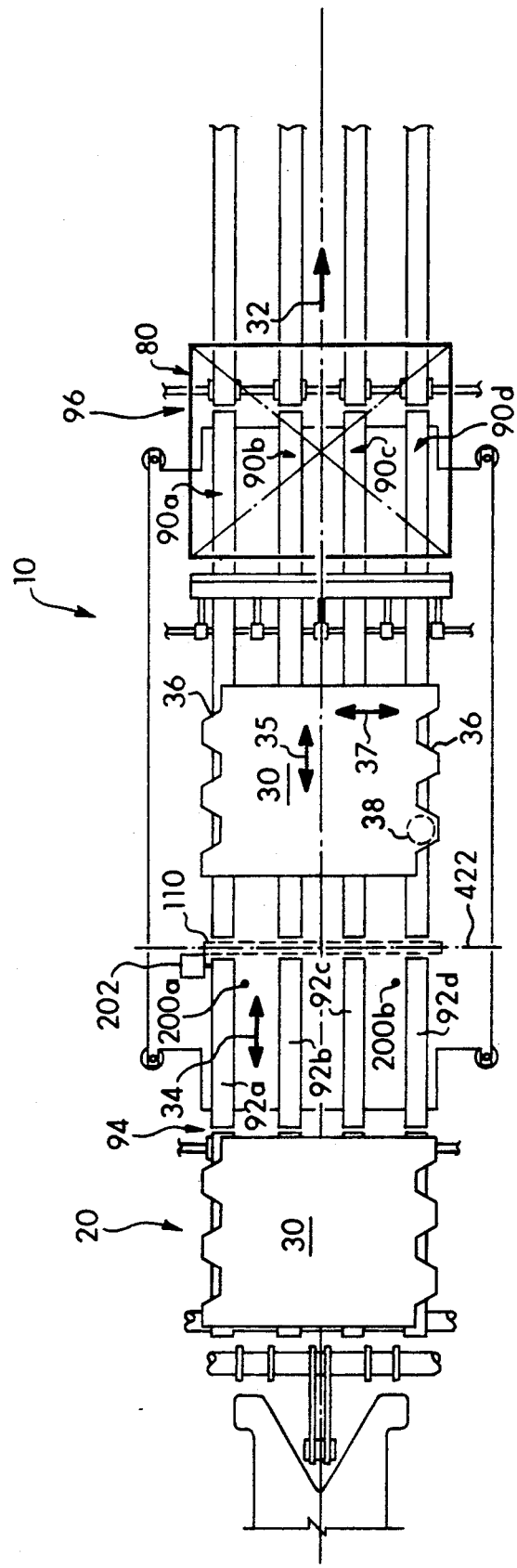
FIG. 2 is the top view of the production line of FIG. 1.

In FIGS. 1 and 2, the optical sheet inspection system 10 of the present invention is shown. The optical sheet inspection system 10 retrofits into a conventional production line 20. In the production line 20, a plurality of sheets 30 are moving in the direction of arrow 32. These sheets are typically moving at a velocity up to 500 feet per minute and with spacings 34 between sheets of a foot or more. The system 10 of the present invention will accept scrolled sheet widths 37 from 21 inches to 44 inches and lengths 35 from 28 inches to 38 inches. The maximum sheet width 37 for non-scrolled sheets is 42 inches. The present invention, however, is not to be limited to such dimensions and these sheet sizes are those for a preferred embodiment.

In the production line 20, the sheets may be delivered from a conventional unit such as a wicket 40 which hangs each sheet for drying after coating. The wicket 40 delivers the sheets to an acceleration conveyor 50 which, in turn, delivers the sheets onto the optical sheet inspection system 10 of the present invention. After optical inspection, the sheets are then delivered onto a conventional conveyor 60 for delivery into, for example, a stacker 70. It is to be expressly understood that the wicket 40, the conveyors 50 and 60, and the stacker 70 are conventionally available in production lines for conveying sheets 30. The optical sheet inspection system 10 of the present invention is designed to retrofit into an existing production line and to produce a full pixel-by-pixel video image of each individual sheet 30. As shown in FIG. 2, the sheets may have scrolled edges 36 or they may be fully rectangular in shape without scrolled edges. The scrolled edges 36 are designed such that each outwardly extending substantially trapezoidal shape is designed to make one can or can lid (as shown by dotted lines 38). When a defect, typically greater than 0.070 inches in size, is detected on the underside of the sheet 30, the optical sheet inspection system 10 of the present invention places the rejected sheet in a reject tray 80. If no defect is detected, the fully inspected sheet is delivered onto conveyor 60 and into, for example, a stacker 70.

As shown in FIGS. 1 and 2, four separate conveyor belts 90 and 92 are utilized to deliver the sheets 30 through the production line. The mechanics for delivering these sheets through the production line and through the optical inspection system 10 of the present invention are well known and may comprise any of a number of different approaches.

The optical sheet inspection system 10 of the present invention is designed into a frame 100 having a formed viewing window 110 over which each sheet 30 is delivered by the conveyors 92. The formed viewing window 110 has a length perpendicular to the direction of movement 32 and this length is greater than the width 37 of the sheet 30. The conveyor belts 92 receive each individual sheet from the acceleration conveyors 50 in order to deliver each of the sheets over the formed viewing window 110. A bank of high intensity lights 120 direct diffused light 130 into the formed viewing window 110. The directed light is reflected off the bottom surface of each individual sheet 30 and the reflected light 140 is optically delivered into cameras 150. The cameras 150 capture a high resolution video image of a line across the width 37 of the bottom surface 39 of each sheet 30 so that as the sheet moves across the viewing window 110, a plurality of lines are captured so that a video image of the undersurface 39 of sheet 30 can be formed.

As shown in FIG. 1, the reflected light 140 is delivered into a housing 160 through a transparent window 162. The reflected light is bent by mirror 164 which redirects the light through an infrared filter 166 and into the cameras 150. It is to be expressly understood that the configuration, the orientation of the cameras 150, the IR filter 166, the mirror 164 and the window 162, the housing 160, and the optical path 130 and 140 can vary under the teachings of the present invention. For example, a variation could place the camera directly in path 140 without bending the optical path with mirror 164.

In addition, as shown in FIG. 1, a system control 170 is provided which controls the overall operation of the optical sheet inspection system 10 of the present invention. The system control 170 is interconnected with an image analysis apparatus such as the FASTTRACK ® analyzing system which is commercially available from Ball Corporation. The system control 170 is interconnected with the cameras 150 to store the electronic video image of each individual sheet as obtained by the cameras. Once the first subimage is obtained, the image analyzer conventionally commences to evaluate the image for the presence of defects. This total image is actually formed by a multiplicity of subimages (up to 12). The subimages have a format so that a conventional image analyzer can analyze the image for defects.

The analysis of the total image for a given sheet must occur rapidly so that the sheet can be rejected and placed in tray 80 when a defect is found. When a defect is detected, the system control 170 activates the reject mechanism 82 to place the rejected sheet 30 into the reject tray 80. It is to be noted that the optical sheet inspection system 10 of the present invention is capable of scanning each individual sheet 30 as it moves over the formed viewing window 110 in order to capture a line-by-line image of the bottom surface of the sheet 30 for delivery into the system control 170 and image analyzer 180. The image is then analyzed and in the presence of a defect greater than a certain predetermined size, the reject mechanism 180 is activated to reject this sheet in sufficient time to place the sheet in the reject tray 80.

In the example of FIG. 1, the following types of defects are detected on the underside of sheet 30: spots in the applied coating, grease, metal laminations, scratches, wicket marks, and soot.

The system 10 is built into a welded frame 100 with both castered wheels and adjustable hard mounted feet 102. The wheels allow easy movement of the machine in a plant and the adjustable feet 102 provide for height adjustment in the production line.

It is to be expressly understood that the present invention is not to be limited to the size of the sheets, the configuration of the edges, the nature of the coatings, the position in the production line, or the use of a particular image analyzer.

The details of the present invention will now be discussed.

High Intensity Diffused Illumination

Figure 3:
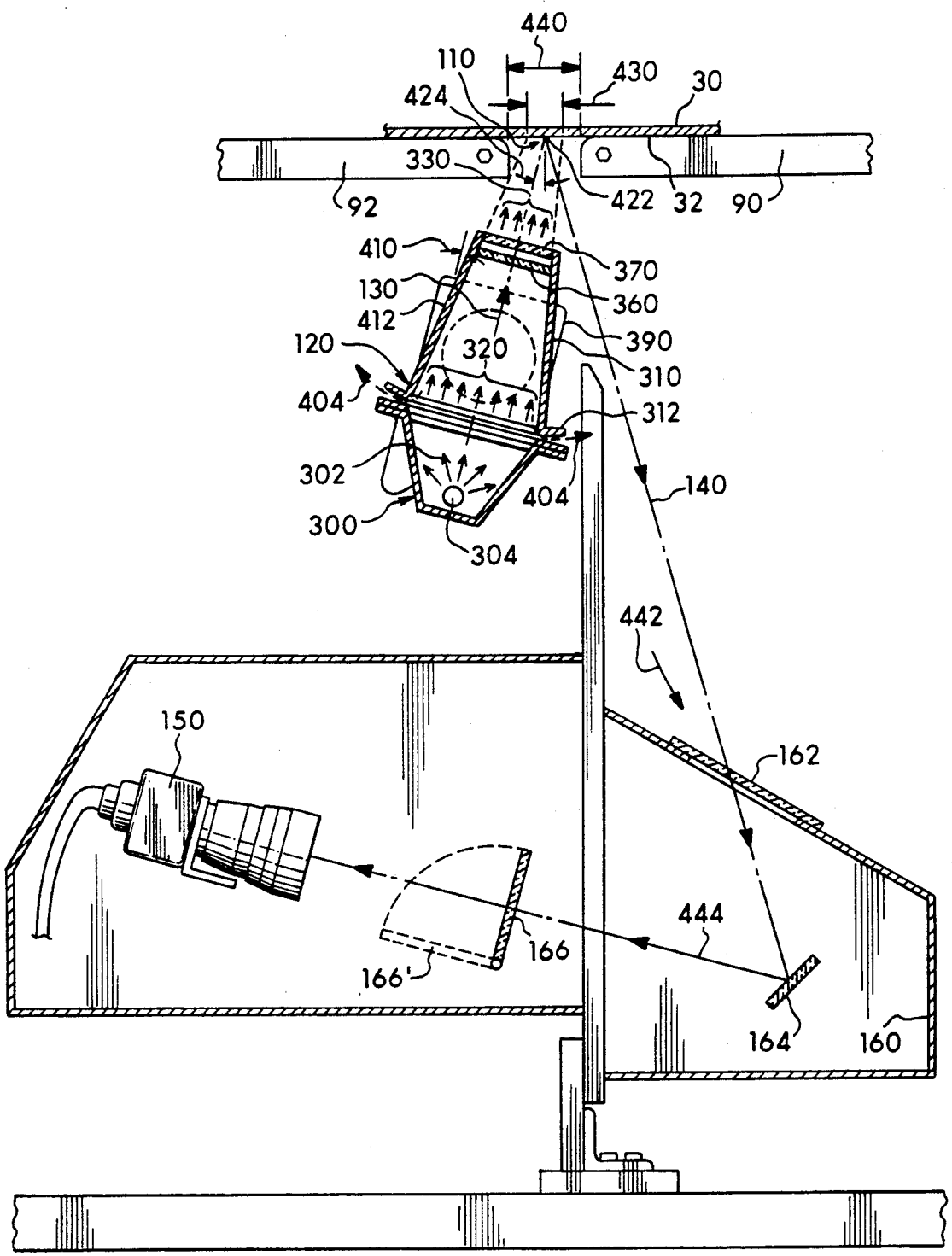
FIG. 3 is a cut-away side view of the optics of the present invention.
Figure 4:
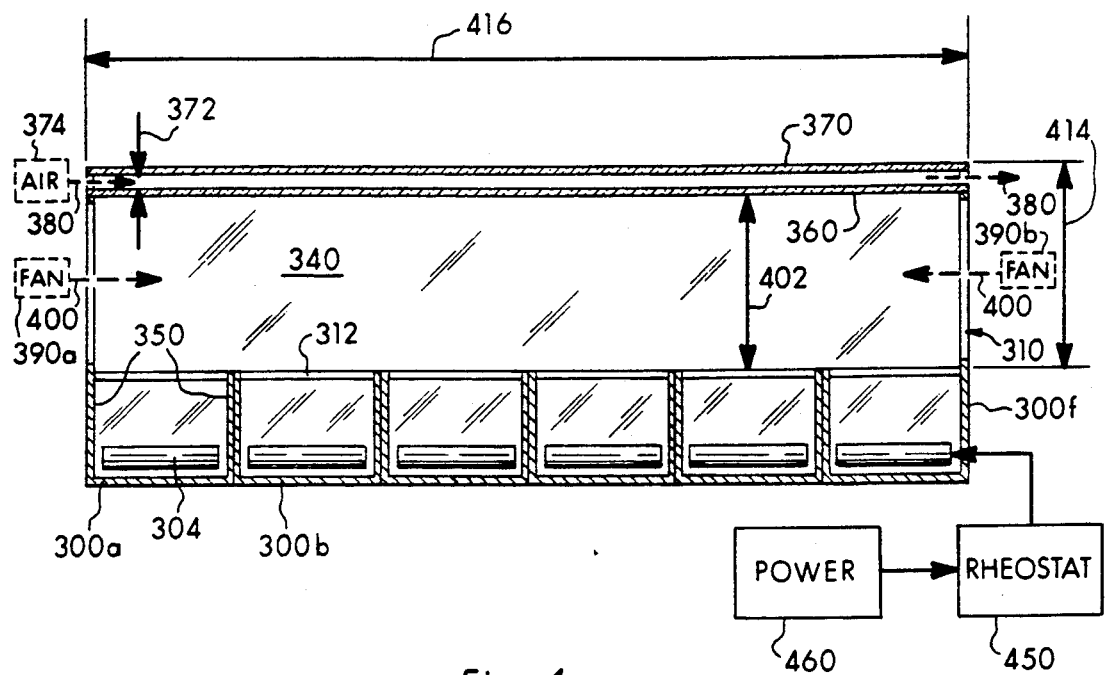
FIG. 4 is a cut-away side view of the bank of lights used in the optical inspection system of the present invention.

In FIG. 3, the source 120 of illumination is set forth to include a number (e.g., six) of lamps 300a-f such as 500 watt halogen lamps. Each lamp 300 is stacked as shown in FIG. 4 to provide an output of three kilowatts of light into the viewing window 110. With an individual sheet moving at 500 feet per minute, or 100 inches per second, the time it takes to capture a line in the video image is 0.3 milliseconds. Stated otherwise, a line of video is captured for each 0.030 inches of sheet traveling over the viewing area 110. A high intensity light source 120 uniformly applied in the viewing window 110 is required to capture the video image. If the individual sheets were moving 1000 feet per minute, then 6 kilowatts of light would be required to enable the cameras to satisfactorily capture an image. For the desired resolution required of one video line per 0.030 inches and at sheet speeds of 500 feet/minute, a high intensity light source is required. The intensity of the light is a further function of the reflectivity of the surface being examined. If the sheet is more reflective, then the electrical power to the lamps 300 can be selectively cut down through use of a rheostat controlling the power 460. Coatings having greater reflectivity require less intensity of light.

In the preferred embodiment for each 0.030 inches of sheet movement a high resolution line image is generated. A typical 36 inch sheet will have at least 1200 lines of information in its overall image.

In FIGS. 3 and 4, the halogen lamps 300 are interconnected to each other to form a bank of adjacent lamps. In the preferred embodiment, six lamps 300a14 300f are utilized, but it is to be expressly understood that a number of lamps greater or lesser than six could also be effectively utilized.

Attached to the light output of the bank of lamps 300 is a light box 310 which is specially constructed to maximize the intensity of light 330 being delivered out from the light box 310 and into the formed region 110 based upon the input light 302 from the lamps 300. The light box contains a highly polished mirror-like surface 340 on all internal sides to the light box. The mirror surface 340 is obtained by highly polishing aluminum material into a mirror surface.

In addition, under the teachings of the present invention, the internal side surfaces of each lamp are also provided with a highly polished mirror surface such as made from aluminum material. Commercially available halogen lamp housings do not have mirror-like sides 350 and are modified under the teachings of the present invention. Hence, all surfaces in each lamp housing 300 and in the light box 310 have mirror finishes. This increases the internal reflection of the light 302 from each halogen bulb 304 and concentrates the light 330 into the formed region 110.

At the upper end of the light box 310 is a clear, heat resistant glass plate 360 and above that is positioned a diffuser 370. The diffuser 370 is preferably made from opal glass but acrylic materials may also be used. An air space 372 exists between plates 360 and 370. The air space 372 provides a pathway for delivering air 380 between plates 360 and 370. Air is delivered in a conventional fashion from a source 374 such as by means of a blower through the air space 372 in order to remove heat buildup caused by light 320 so as to prevent the acrylic diffuser 370 from melting. In addition, fans 390a and 390b are utilized to blow air 400 through air space 402. Opposing fans 390a and 390b are used to deliver air into space 402 and the delivered air is selectively removed at the formed juncture opening 312 of the light box 310 and the lamps 300 as shown by arrows 404 in FIG. 3. The heat in space 402 does not buildup significantly and the air flow 400 from fans 390 is sufficient to keep the heat at a manageable level such as under 500° F. It is to be expressly understood that while the present invention provides two air paths 380 and 400 for the removal of heat buildup in the source of illumination 120, other suitable approaches could also be utilized to cool the source of illumination 120. For example, cooling lines such as plumbing carrying coolant could be installed or air pathways of different shapes and configurations could be utilized.

In summary, in order to obtain the maximum intensity of the light 330 coming from the light box 310, the light box is designed to have mirrored surfaces on all sides and each lamp housing had its ends 350 provided with a mirrored surface so that the maximum amount of light 330 is obtained from the generated illumination 302 as is possible.

In the preferred embodiment, the glass 360 is typically ¼ inches thick. The diffuser 370 is typically ⅛ inches thick and is of commercial grade in quality.

The angle 410 of the sides 412 of the light box 310 is preferably in the range of 10°. This angle is such that it provides a maximum amount of diffused light 330 output into the formed viewing window 110. In the preferred embodiment, the height 414 of the light box 310 is 6 ½ inches and the length 416 is 56 inches. The plates 360 and 370 are suitably connected to the light box by means of a groove. The center line of the illumination 330 hits the line 422 on the underside 32 of a sheet 30 which corresponds to the line to be captured by the video cameras. As shown in FIG. 3, and in the preferred embodiment, the light 330 is directed at an angle 424 of about fifteen degrees. The reflected light 140 at the same angle is delivered downwardly into the housing 160 as previously discussed.

In FIG. 3, the viewing window has a width 430 which is less than the gap width 440 between adjacent conveyors 92 and 90. As shown in FIG. 3, the source of illumination 120 delivers high intensity diffused light 330 into a viewing window 110 through gap 440 in the production line to illuminate the undersurface 32 of a moving sheet 30. No interference with the light from the conveyor belts 90 or 92 or any other part of the production line occurs. Hence, any defects on surface 32 whether the surface is coated, without coating, or otherwise, is fully illuminated with high intensity diffused light 330. Any heat buildup within the system 120 is selectively removed by fans and air delivery systems. This also removes any dust that may be present since the air is thoroughly filtered when delivered through the light box 414.

In the preferred embodiment, the width of the gap 440 is about two and three-quarters inches and this width is designed so as to prevent drooping of the leading edge of a sheet of 0.003 inch steel as it moves across the gap 440. It is to be expressly understood that the present invention is not limited to a gap of two and three-quarters inches but that the gap can be suitably designed based upon the thickness of sheet 30 and a desire to prevent drooping of the sheet as it travels across opening 440. In the preferred embodiment, the diffuser plate 370 is spaced about four inches from the undersurface 32 of the sheet 30.

The reflected light 140 is delivered downwardly into housing 160 through a transparent window 162 which is made from glass. To prevent dust buildup on glass 162, air 442 is delivered across the upper surface of the glass 162. The delivery of air 442 can be accomplished by a number of conventional means such as by means of a blower fan, etc. Of course, the angular length of the glass 162 is sufficiently long to permit all of the reflected light 140 in the field of view of the cameras to be delivered into the inside of housing 160. The reflected light 140 strikes a front surface of mirror 164 which turns the reflected light 140 and redirects it along path 444 into camera 150. Again, the mirror 164 is sufficiently long to fully redirect light 140 along path 444. Disposed in path 444 is the infrared filter 160. Filter 166 is of the same angular length as mirror 164. Filter 166 can be selectively pivoted into path 444 as shown in FIG. 3 or pivoted out of the path as shown by 166'. The infrared filter 166 selectively enhances defects such as slow change defects (e.g., a feathered smear). The housing 160 is enclosed in order to prevent dust from the rather dirty environment of a production line from interfering with the sensitive camera optics of the present invention. The pressure of the air in the interior of housing 160 is slightly greater than the atmospheric pressure so as to keep dust from migrating in.

It is to be expressly understood that the dimensions and materials set forth above are preferable and that other suitable dimensions and materials may be used under the teachings of the present invention.

Camera and Optics

Figure 5:
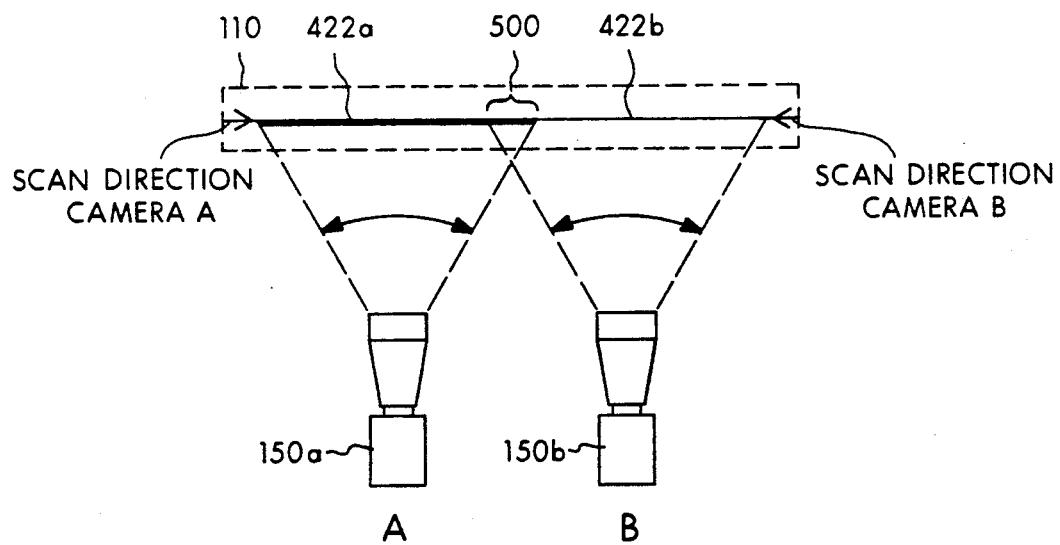
FIG. 5 is an illustration showing the viewing overlap by the two cameras of the present invention.

As shown in FIGS. 3 and 5, two cameras and their respective optics (mirror 164 and filter 166) are housed in an optical enclosure 160. The optical arrangement for both cameras are identical. Each camera 150 includes a F1.4 35 MM lens, an infrared filter 166 that can be selectively placed in the optical path 444 or out, and a mirror 164 to fold the optical path and a window 162. The cameras are preset to operate at the highest sheet transfer velocity with the dullest image on a sheet.

The information on each captured video line is made up of a multiplicity of individual picture elements called pixels. Each of these pixels is generated by a photodiode in the camera. The photodiode stores the light energy focused on it and when read out is a direct indication of the brightness level on the sheet. The electronic image contains 1024 pixels on each line 422a and 422b for each camera 150a and 150b. An overlap area 500 exists between the two cameras. Each pixel represents a width of 0.030" in the direction of width 37. This video from the two cameras provide the capability of forming a stored video image of a sheet with a pixel resolution 0.030" by 0.030".

It is to be expressly understood that the teachings of the present invention are not limited to the use of two cameras and that one camera or three or more cameras could be utilized depending upon the size of sheet 30 and the camera's field of view.

Storage of Video Image

The optical sheet inspection system of the present invention incorporates a unique storage arrangement of the imaged data which eliminates the requirement of special masks dependent upon the configuration of the sheet 30. This unique approach is shown in FIGS. 6a-6d which illustrates the steps of scanning, line capturing, storage of the captured image, and analysis of the stored image.

1. Scanning

Under the step of scanning, as shown in FIG. 6a, a sheet 30 containing defects 644a and 644b is moved in the direction of arrow 32 on the conveyor belts 90 and 92 over the formed opening 110. At time $t_0$, the leading edge of the sheet 30 coincides with line 422 in the window 110 and an image of the line at the leading edge is captured which is shown as line $t_0$ in the line capture step. As shown for $t_0$ in the line capture step, the grey level image is of consistent value across the width 37 of the leading edge.

2. Line Capture

Under the teachings of the present invention and as shown in the line capture step of FIG. 6b, the video image at $t_0$ is generated from cameras A and B. The initial image is low 600a (indicated off-sheet) and immediately steps, at 610a, to a high or maximum grey level 620. This is to be expected since the video image at $t_0$ undergoes a significant transition 610a when commencing to scan the edge of the sheet (i.e., from dark (no reflection) to light (reflection)) and continues until the camera line is full. Likewise, camera B scans right to left until the line is full generating overlap 500.

When sheet 30 is positioned, at $t_1$ over imaging line 422, the scan across the sheet 30 is shown in FIG. 6a as 640. This results in a captured line shown as $t_1$ in FIG. 6b. Note that line $t_1$ has the initial abrupt transition 612a occurring at the same place as the transition 610a for time $t_0$. At time $t_1$, the captured line shows a value change 645a in grey level which corresponds to the presence of a defect 644a in sheet 30. But for the presence of this defect 644a the captured line image at $t_1$ corresponds to that obtained at $t_0$. For this illustration, the defect 644a is a linear defect parallel to the movement of travel 32 as shown in FIG. 6a. The presence of the defect affects the reflectivity of light 140 by decreasing the intensity of reflection. Likewise, camera B, at time $t_1$, captures its half of line 640 as shown in FIG. 6b. This image of the line shows the presence of defect 645b and the edge transition 612b.

As the sheet 30 moves in the direction of 32, and when line 646 in the sheet is over the imaging line 422 at time $t_2$, the cameras capture the image shown at $t_2$ shown in FIG. 6b. Because of the scrolled edge 36 the low intensity region is extended before undergoing transition 614a. Again, an image 647a corresponding to the presence of defect 644a appears. Camera B undergoes the edge transition at 614b and the presence of defect 644b is shown at 647b.

In the line capture step of FIG. 6b, camera A produces that portion of the captured image as shown by line 422a which results in a video image having a low level (off sheet) 600a, the transition 610a, and the high level 620a (on sheet). Camera B produces the image as shown by line 422b which results in a video image having a low level of 600b, the transition 610b, and the high level 620b. The area of overlap 500 is also shown. The field of view for each camera at the sheet inspection plane 442 is 30.7 inches. The fields of view of the cameras overlap the center line by 6.1 inches and extend out from the center line by 24.6 inches.

3. Storage

In the storage step of FIG. 6c, the captured video lines 422a and 422b from cameras A and B are selectively stored in respective memories 660a and 660b. The electronics performing this function will be discussed later. However, the approach to memory storage constitutes an important part of the present invention in that regardless of the shape of the edges 36 of the moving sheet 30, the information stored in memory is "transition edge adjusted" thereby storing all captured video images, regardless of edge configuration, into a rectangular stored image in memory. This transformation is accomplished as follows.

In the storage step of FIG. 6c, memories 660a and 660b are utilized. A beginning storage location 662a for camera A is memory 660a and 662b for camera B is assigned in memory 660b. Hence, when camera A captures the leading edge of the sheet at $t_0$, in the storage step, the transition 610a is aligned with the starting address 662a in memory 660a. The data is then stored for the remainder of the line. Likewise, when camera B captures the leading edge of the sheet at time $t_0$, the captured video image line is stored in memory with transition 610b being placed at starting location 662b in memory 660b. The same process occurs for line 640 on sheet 30 which is scanned at time $t_1$. The defects 644a and 644b are shown, as an illustration as 645a and 645b, respectively. It is to be understood that the graphical representations for memory 660 shown in the storage step are for purposes of illustration only and that the corresponding grey scale digital values (256 different values) would be stored for each pixel. The transitions 612a and 612b for line 640 are shown in FIG. 6b and are also stored at starting addresses 662a and 662b respectively. Notice that the defect 644a is shown at time $t_1$ in image area 645a and is correspondingly stored in memory as shown in FIG. 6c. Likewise, the defect 644b is shown at time $t_1$ in image area 645b and is correspondingly stored in memory as shown in FIG. 6c.

Importantly, at time $t_2$ when line 646 of sheet 30 is scanned by cameras A and B, the transition edges 614a and 614b are also stored at the starting locations 662a for camera A and at 662b for camera B. Hence, the transition edges 614a and 614b are aligned in memory at the same initial address 662a for camera A and 662b for camera B. Again the presence of the defects 647a and 647b are appropriately stored in memories 660.

This storage results in the rectangular transformation of the edges of the optically scanned video images. Regardless of the shape of the edge 36 of the sheet 30, the scanned line images from camera A and camera B will always be stored in a rectangular format. No masks need to be utilized since the transition edge is used to start storing pixel values at the starting location in memory.

4. Analysis

As shown in the analysis step of FIG. 6d, if the stored video images in memories 660 are read out and viewed as video images 670a and 670b, the rectangularization of the sheet 30 distorts the viewed image 670 so that the defects 644a and 644b, as shown in FIG. 6d are distorted according to the configuration of the edge 36. From a defect analysis point of view, a defect is a defect no matter what its shape and any distortion caused to the image 670 by the storing process of the present invention is immaterial since a defect will cause the sheet to be rejected. Hence, sheets 30 having any conventionally shaped edge 36 including a linear edge can be fully handled by the optical sheet inspection system of the present invention.

The storage technique of the present invention automatically causes the sheet portion of the video scanned lines to be stored at the same starting location in memory 660 at the transition edges 610, 612 and 614 for camera A and for camera B. The scroll or whatever configuration of the edge is thereby removed from the stored video image. Hence, no mask individually customized for an individual sheet 30 is required and the system need not be modified for sheets having different edges.

The area of overlap 500 is set to accommodate the maximum scroll depth of sheets as well as the offset of the sheet from the center line, and the amount of skewness of the sheet on the conveyors. The maximum combination of offset and skewness is a function of the overlap 500 of camera fields of view. If this combination is too large, there will be an insufficient number of pixels from one of the cameras to complete one of the subimages. This condition is detected and inspection of the sheet is terminated. Should the sheet 30 be inspected, it could be rejected even though it had no flaws.

It is to be understood that a number of different memory configurations could be utilized to store the pixel grey level values under the rectangularization concept of the present invention.

SHEET SENSING

As shown in FIG. 2, sheet sensors 200a and 200b are utilized to sense the leading edge of each sheet 30 as it approaches the formed viewing window 110. An encoder 202 is connected to the master drive for conveyors 90 and 92 to generate a series of output pulses which pulses are proportional to the speed that the conveyors are moving and each pulse represents a distance traveled, i.e., one pulse for each 0.030 inches of travel on conveyors 90 and 92. The encoder 202 can be interconnected with the conveyor in a number of conventional approaches to generate an output of pulses.

Figure 7:
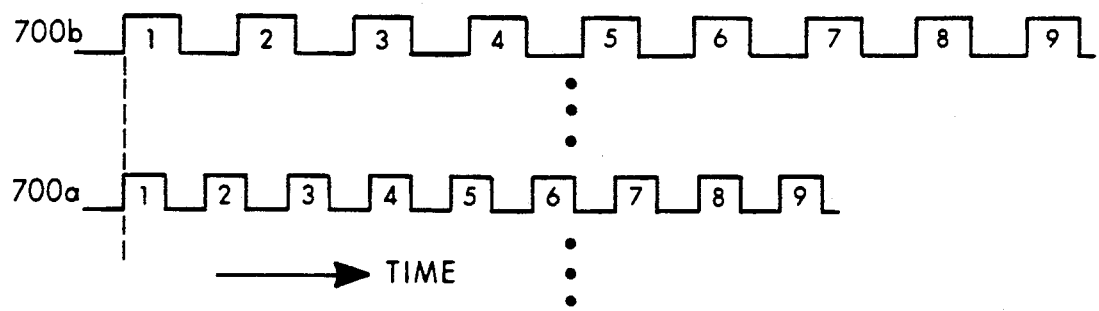
FIG. 7 is a graph illustrating the encoder pulse technique of the present invention.

In FIG. 7, the encoder pulses 700a are generated at a first conveyor speed and encoder pulses 700b are generated at a second conveyor speed. Regardless of the speed of the conveyors (or of the sheet 30), the distance from the sensors 200 to the capture line 422 will be represented by a fixed number of pulses. As shown in FIG. 7 and for purposes of illustration only, the first speed represented by encoder pulses 700a generates nine encoder pulses to go the same distance as the slower speed as represented by encoder pulses 700b. The same distance is traveled upon the completion of the ninth encoder pulse for each pulse stream.

This is an important concept under the teachings of the present invention. Hence, in reference to FIGS. 1 and 2, each individual sheet 30 moves in the direction of arrow 32 in the production line. When the leading edge of the sheet 30 engages sensors 200a and 200b, the electronics of the systems, to be discussed later, counts a predetermined number of encoder pulses from encoder 202 (corresponding to a fixed distance). When the predetermined number is detected, cameras A and B precisely capture the first complete line on the leading edge of the sheet. This provides an exact spacing delay that is independent of conveyor speed. It is clear that through the use of sensors 200, encoder 202, that cameras A and B will commence capturing images regardless of the speed of the conveyors in the production line and regardless of the spacing between the individual sheets. The synchronization of the cameras 150 to the sheet 30 position permits the system to operate independently of sheet velocity.

PROCESSING OF SKEWED SHEETS

Sensors 200a and 200b also enable the system of the present invention to continue defect analysis and optical imaging despite misalignment or skewness of the sheet up to a predetermined amount of skewness. This is illustrated in FIGS. 8a and 8b.

Figure 8A:
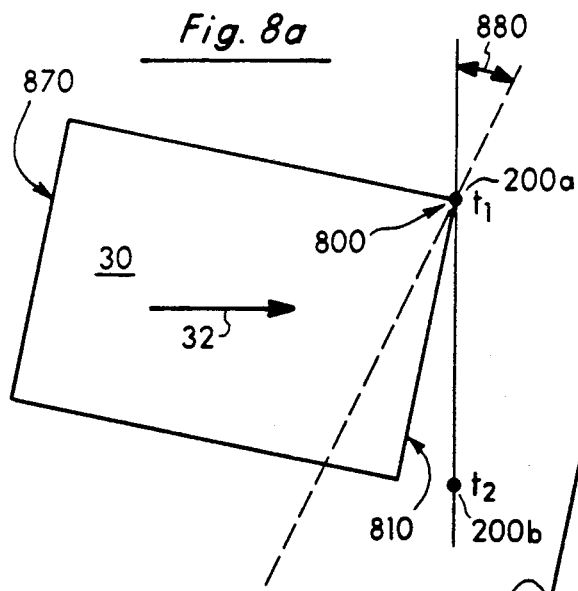
FIGS. 8a and 8b are diagrams illustrating how the present invention is capable of analyzing sheets that are misaligned or skewed as they are delivered in the production line.
Figure 8B:
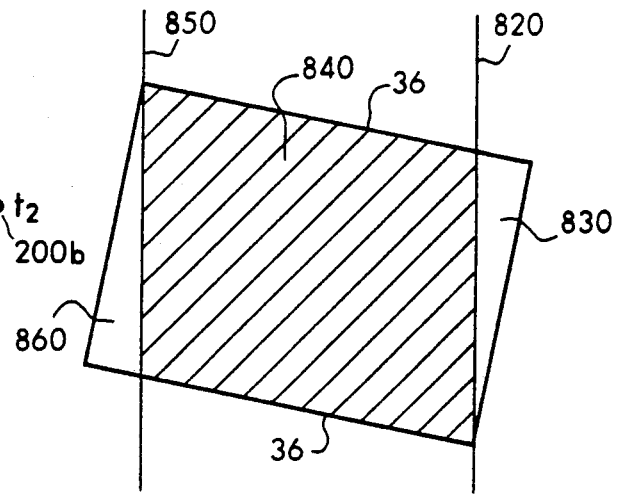

In FIG. 8a, a skewed sheet 30 is being delivered in the production line in the direction of arrow 32. Tip 800 on the leading edge of sheet 30 activates sensor 200a at time $t_1$. A portion of the leading edge 810 will activate sensor 200b at $t_2$. The electronics of the present invention do not start counting the encoder pulses of FIG. 7 until both sensors 200a and 200b are activated. Therefore, as shown in FIG. 8b, the first image line captured by cameras A and B is line 820. Thus, a portion 830 of sheet 30 is not optically imaged. If a defect resides in this area 830, it will not be detected by the optical imaging system of the present invention. However, the area 840 will be fully optically imaged and analyzed for defects. The end of the imaging occurs with line 850 and hence area 860 of sheet 30 is also not optically inspected. Hence, when lagging edge 870 of the sheet is detected by sensor 200a, after a spaced delay (as determined by the encoder pulses) cameras A and B are deactivated so as to miss area 860. It is not possible to inspect areas 830 and 860 under the teachings of the present invention, since to do so would cause an automatic defect. However, even though the sheet is skewed and the side edges 36 of the sheet 840 are tilted, under the rectangularization of the stored image, as discussed previously, the remaining portion 840 of the image can be fully analyzed for defects.

Under the teachings of the present invention, the present invention is able to handle skewnesses up to an angle 880 of about five degrees. Hence, if the sheet is too skewed, inspection of the sheet may be defaulted which precludes a rejection. However, if the sheet is not too skewed, only a portion of the leading and lagging edges are not inspected. Importantly, the optical imaging system of the present invention permits inspections of skewed sheets which under conventional approaches simply would not be inspected.

ELECTRONICS

Figure 9:
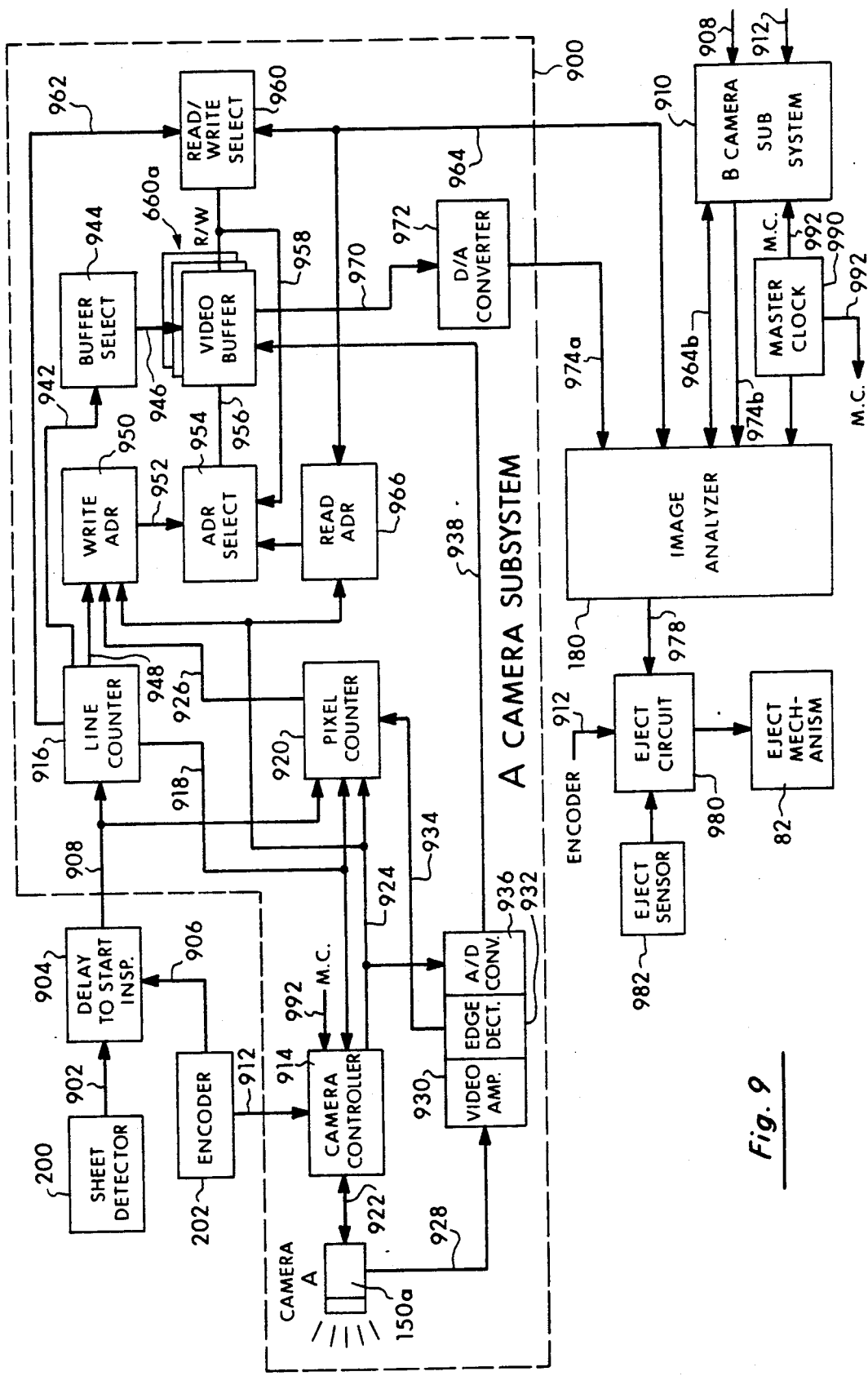
FIG. 9 is a block diagram of electronic control of the present invention.

In FIG. 9, the electronics for operating the optical inspection system of the present invention is set forth. FIG. 9 illustrates an "A camera subsystem 900" and a "B camera subsystem 910." The following discussion pertains only to the A camera subsystem 900 with the understanding that the B camera subsystem 910 contains the same circuitry.

The sheet detector 200 which is composed of the two separate sensors 200a and 200b sends signals over lines 902 to a delay to start inspection circuit 904. Circuit 904 is further interconnected to the encoder 202. The encoder 202 delivers the series of pulses set forth in FIG. 7 over line 906 to the delay to start inspection circuit 904. Circuit 904 functions upon receipt of a sheet detected pulse on line 902 from the sheet detectors 200 to start counting the pulses appearing on line 906. When a predetermined number of pulses have been counted (i.e., directly corresponding to a predetermined amount of distance traveled by the sheet 30), an activation signal is generated on line 908. It is this signal that activates the camera A subsystem 900 and the camera B subsystem 910 to start recording. The encoder 202 also delivers its pulses over line 912 to the camera controller 914. Signals on lines 908 and 912 are also delivered to the B camera subsystem 910 as shown in FIG. 9.

The A camera subsystem 900 functions as follows. Line counter 916 receives the sheet activation signal on line 908. It immediately issues a start-of-line command on line 918 to the camera controller 914 and to the pixel counter 920. The camera controller 914 interconnected to the camera over lines 922 causes the camera 150a to start scanning a line. Camera controller 914 also receives the encoder pulses from encoder 202 over line 912. Hence, the camera controller first responds to an encoder pulse to start a scan and, therefore, with each encoder pulse, the camera commences a scan. However, the start-of-line command on line 918 causes the camera controller to capture the scanned video image. The number of pixels are delivered over line 924 from the camera controller (i.e., from a pixel clock internal to the camera 914 controller). The pixels are only counted by circuit 920 after the receipt of a transition edge detect signal 934 from the detection of the transition edge. Hence, when the pixel counter counts up to a predetermined number of pixels it provides the width of the stored line, and an end-of-line signal is generated on line 926.

Hence, it can be observed that the camera controller 914 starts each scan with the presence of an encoder pulse from the encoder 202, but only in the presence of a start-of-line command on line 918 are the images to be stored. The start and end-of-the line of stored video is determined by the pixel counter 920 which thereupon counts the pixels to a predetermined number and issues an end of line signal on line 926.

Hence, camera A is properly activated by the camera controller 914 to start producing, pixel by pixel, a line video image for delivery over line 928 and into a video amplifier 930. The video amplifier is connected to a transition edge detector 932 which detects the edges as discussed and illustrated with respect to FIG. 6 in the line capture step. The edge detector 932 detects the transition edges—i.e., 610, 612 and 614 of FIG. 6. When such an edge is detected, a suitable output is delivered over line 934 to the pixel counter 920 to start the counter 920 counting. When the counter 920 commences to count, for the first time, the captured line image is stored in video buffer 660 as will be explained later. However, it can be observed that even though the location of the transition edge varies on the sheet 30, the storage of the line commences with the detection of the transition edge by circuit 932 which starts counter 920. The analog to digital converter 936 converts the analog signal into digital values and delivers those values on line 938 to video buffer or memory 660a.

In the preferred embodiment, the line counter 916 and the pixel counter 920 are conventionally designed pulse counters. The camera controller 914, video amplifiers 930, A to D converters 936, and the edge detector 932 use conventionally designed circuits. The camera 150 is a Fairchild Model No. CAM1830.

At this stage in the operation of the electronics shown in FIG. 9, the camera controller has been properly activated to record the first line (i.e., the leading edge of the sheet 30) and to deliver a digital signal on line 938 into memory 660a.

Memory 660a operates in the following fashion. The line counter 916 and the pixel counter 920 are used to form the address for storing the digital values for each line in memory 660a. The line counter 916 delivers the lines being counted over line 942 to a buffer select circuit 944. In the embodiment of FIG. 9, a number of video buffers can be utilized in the subsystem 900 for camera A. Each video buffer 660a contains the same number of lines and, therefore, the buffer select 944 selects the next buffer to be written to when the prior buffer is full as determined by the line counter. Buffer select circuit 944 simply selects over lines 946 the proper video buffer 660a.

The specific address for the stored line is generated by the WRITE address circuit 950. Hence, the line counter outputs its count over lines 948 to the WRITE address circuit 950. The WRITE address circuit 950 also receives control signals from the pixel counter 920 over lines 926. These signals function to form the specific address for data storage within a buffer of memory 660a. After formation, the address is then delivered over lines 952 to the address select circuit 954 for delivery of the address over lines 956 to the memory 660a. Hence, the address select circuit 954 can either deliver an address for writing memory 660 from circuit 950 or deliver an address reading information from memory 660a from circuit 966. The state of operation is controlled by the read/write pulse appearing on line 958 from the read/write select circuit 960.

During the capture step and the storage step as illustrated in FIGS. 6b and 6c, the read/write select circuit 960 is a WRITE command to memory 660. Hence, each line and each pixel in each line is selectively stored in memory 660a as discussed above.

During the analysis step as shown in FIG. 6d, the stored video information in memory 660 must be quickly read out in sufficient time so that if there is a defect, the sheet can be rejected. Hence, the information must be read out from memory and analyzed by the image analyzer 180 in sufficient time to operate the eject mechanism 82.

The reading of the image data from memory 660a occurs as follows. When the line counter 916 determines that a buffer is full, it outputs signal 962 to the read/write select 960. This enables the read/write select to select the last filled buffer to be read upon receipt of synchronizing signal 964 from the image analyzer 180. The read/write select circuit 960 is activated over lines 964 to be in the READ mode. A READ address circuit 966 is also interconnected with line 964 and also becomes activated. The pixel clock on line 924 causes the read address circuit 966 to sequentially deliver, pixel by pixel, all information stored in memory 660 starting with the first pixel of the first line (i.e., starting with transition edge) to the last pixel of the last line. The stored information is delivered out from the memory 660 over lines 970 to a D to A converter 972. The received digital information from memory 660 is converted into an analog value for delivery to the image analyzer 180. As mentioned, the image analyzer 180 is the conventionally available FASTRACK processor commercially available from the Ball Corporation, 345 South High Street, Muncie, Ind. 47307. This information from the D to A converter 972 is delivered over line 974a. Correspondingly, a similar signal is delivered on line 974b from the B camera subsystem 910. New lines are requested over line 964. The FASTRACK processor 180, in the conventional fashion, analyzes the information for the presence of a defect and in the presence of a defect issues a reject signal on line 978 to the eject circuit 980.

The image analyzer 180 alternately selects filled buffers from the camera subsystems 900 and 910 for processing as buffers are being filled. Reject signals may be generated in the analysis of data from any of the buffers. In the inspection of a given sheet up to 12 buffers of data are used in the preferred embodiment, six from each subsystem.

The eject circuit 980 activates the eject mechanism 82 to cause the sheet 30 containing the defect to be placed into tray 80. The eject circuit outputs an eject signal to the eject mechanism when the leading edge of sheet to be rejected is detected by the eject sensor and a reject signal 978 has been received from the image analyzer. The eject signal remains high for an adjustable number of encoder pulses through the means of a conventional counter in the eject circuit.

A master clock 990 is used to generate master clock signals on lines 992 to the system. In the preferred embodiment the frequency of the master clock is 7.18 MHz. The clock is a conventional oscillator counter device.

METHOD OF OPERATION

The optical inspection of sheets 30 occurs as follows:

A. As shown in FIG. 1, each sheet 30 is transferred in the production line 20 to the optical inspection system 10 at essentially the velocity of the acceleration conveyor belts 50 and are generally well aligned to the conveying direction 32. As mentioned, the optical inspection system 10 can accommodate some skewness of the sheets.

B. Each sheet 30 travels down the conveyors 92 to sheet sensors 200a and 200b. If a sheet is completely square to the direction of travel 32, both sensors 200a and 200b will turn on simultaneously. Any skewness of the sheet will cause one or the other sensor to turn on later than the other depending on which direction the sheet is skewed as discussed with respect to FIG. 8. If a sheet is too skewed, the sheet inspection is defaulted.

C. When both sheet sensors 200a and 200b are on, the camera controller 914 as shown in FIG. 9 starts counting encoder pulses on line 912. There is one encoder pulse for each 0.030" of conveyor belt movement. After a preset distance of travel, (i.e., a specific number of encoder pulses as shown in FIG. 7) the leading edge of sheet 30 will be in the full field of view of both cameras 150. At this point, the start-of-line command 918 enables the subsystems to start storing data upon receipt of the first edge detect signal 934.

D. Prior to storing the line of video in memory 660a, the transition edge is determined on the video by the edge detector 932. Storing of the video line occurs at the transition edge (i.e., 610, 612 and 614) as illustrated in FIG. 6c. The effect of this is that the scrolled edge of a sheet is transformed into a straight edge in the composite electronic image in memory 660a which gives the capability of inspecting close to the scrolled edge and eliminates the need for a mask.

E. After the transition edge has been found by circuit 932, video images are digitally stored (8 bits per pixel).

F. The stored video images are then sent to the image analyzer 180. If a rejectable fault if found by the image analyzer in any of the frames of video, a reject signal is generated and sent to eject circuit 980. Circuitry 980 uses the accumulated eject signals (since there may be more than one defect) from a sheet and the sheet presence signal from eject sheet sensor 982 to generate the actuation signal for activating eject mechanism 82. After the eject circuit actuates the eject mechanism, the circuit counts the encoder pulses and maintains the actuation for a selectable number of encoder pulses.

CONVEYING SUBSYSTEM

The conveyors 90 and 92 provide all the functions to move the sheet from input side 94 of the machine to the exit 96 as shown in FIG. 2. Eight individual conveyor units are used—four entrance 92 and four exit 90. All of the conveyor units are direct coupled through drive shafts and drive belts to an induction motor, not shown. In the absence of belt slippage, all conveyor belts will be moving at the same velocity. A position encoder 202 is also belt coupled to the conveyor drive so that belt position pulses are available. An encoder pulse is put out every 0.030" of belt travel as shown in FIG. 7. The system of the present invention has been designed so that these encoder pulses are the master reference for the inspection operation which is independent of conveyor speed. The individual conveyor units are Dornier 4100 series but modified with a belt slip sensor, not shown. This sensor enables the system to determine when a belt is slipping too much and should be replaced.

The induction drive motor is driven by a Toshiba variable frequency motor controller. A display on the control box shows the frequency of voltage being supplied to the motor. The conveyors may be started and stopped with a remote start-stop- switch adjacent to the control panel.

EJECT SUBSYSTEM

The eject subsystem removes defective sheets from the conveyor line. It operates by raising seven shaft mounted fingers 82 into the path of a sheet 30 as shown illustrated in FIG. 1. The sheet momentum plus the force generated by the portion of the sheet still contacting the conveyor 90, drives the sheet up on the fingers 82 into a driven pinch roller assembly 84. The pinch rollers 84 are driven by an induction motor, not shown, with its own variable frequency controller. The pinch roller speed is adjusted to pull the sheet into the reject stack 80. The fingers 82 are rotated through a crank mechanism by a pneumatic linear actuator, not shown. An electric bi-directional valve drives the linear actuator in both directions. The circuitry 82 to control the eject fingers 82 is shown in FIG. 9.

It is to be expressly understood that the claimed invention is not to be limited to the description of the preferred embodiment but encompasses other modifications and alterations within the scope and spirit of the inventive concept.

We claim:

1. A system for optically inspecting high velocity individual sheets having scrolled and unscrolled edges in a production line for defects, each of said individual sheets being at spaced locations from each other and having a first dimension in the direction of movement and a second dimension perpendicular thereto, said system comprising:

a formed viewing window, said formed viewing window having a length perpendicular to said direction of movement and a width greater than said second dimension of each said individual flat sheet;

means receiving said individual flat sheets from said production line at said spaced locations for delivering each of said flat sheets over said formed viewing window at said high velocity, means for uniformly and continuously illuminating the surface of each said individual flat sheet along said length of said formed viewing window with high intensity diffused light as each said individual flat sheet is delivered over said formed viewing window by said delivering means, means receiving the reflected high intensity diffused light from the surface of each individual flat sheet for capturing a video image of each line across said length of each of said individual flat sheet independent of the velocity of each said individual flat sheet, each said line being one pixel wide and a sufficient number of pixels in length to equal said second dimension of each said individual flat sheet, means connected to said capturing means for storing an electronic image of each said individual flat sheet, said electronic image comprising a sufficient number of said captured lines to equal said first dimension of each said individual flat sheet, wherein said storing means is first capable of determining the edge of the first captured video line image and then is capable of storing all subsequent captured video line images adjusted to said determined edge so that any scrolled edge of said individual sheet is transformed into a straight edge in the corresponding electronic image thereby enabling the analysis of any defects present in said scrolled edge, means connected to said storing means for analyzing said stored electronic image of each said individual flat sheet for defects, said analyzing means issuing a reject signal when a defect is detected in said stored electronic image, and means receptive of said reject signal for removing the individual flat sheet corresponding to said reject signal from said production line, means located on said delivering means for detecting the leading edge of each said individual flat sheet before each said individual flat sheet is delivered over said formed viewing window, said detecting means issuing an edge signal, means connecting to said delivering means for generating a stream of encoder pulses corresponding to said velocity of each said individual flat sheet, and means receptive of said edge signal and of said encoder pulses for activating said capturing means after each said individual flat sheet has traveled a preset distance from said detecting means so that the first video line image captured corresponds to the first line on each said individual flat sheet.

2. The system of claim 1 wherein said detecting means comprises two sensors located near opposing sides of said second dimension of each said individual flat sheet.

3. A system for optically inspecting high velocity individual flat sheets having scrolled and unscrolled edges in a production line for defects, each of said individual flat sheets being at spaced locations from each other and having a first dimension in the direction of movement and a second dimension perpendicular thereto, said system comprising:

a formed viewing window, said formed viewing window having a length perpendicular to said direction of movement and a width greater than said second dimension of each said individual flat sheet;

means receiving said individual flat sheets from said production line at said spaced locations for delivering each of said sheets over said formed viewing window, at said high velocity, means for uniformly and continuously illuminating the surface of each said individual flat sheet along said length of said formed viewing window with high intensity diffused light as each said individual flat sheet is delivered over said formed viewing window by said delivering means, means receiving the reflected high intensity diffused light from the surface of each individual flat sheet for capturing a video image of each line across said length of each of said individual flat sheet independent of the velocity of each said individual flat sheet, each said line being one pixel wide and a sufficient number of pixels in length to equal said second dimension of each said individual flat sheet, wherein said capturing means is further capable of capturing said video images even if the delivered individual flat sheet over said formed viewing window has a skewness less than a predetermined acceptable value, means connected to said capturing means for storing an electronic image of each said individual flat sheet, said electronic image comprising a sufficient number of said captured lines to equal said first dimension of each said individual flat sheet, wherein said storing means is first capable of determining the edge of the first captured video line image and then is capable of storing all subsequent captured video line images adjusted to said determined edge so that any scrolled edge of said individual flat sheet is transformed into a straight edge in the corresponding electronic image thereby enabling the analysis of any defects present in said scrolled edge, means connected to said storing means for analyzing said stored electronic image of each said individual flat sheet for defects, said analyzing means issuing a reject signal when a defect is detected in said stored electronic image, and means receptive of said reject signal for removing the individual flat sheet corresponding to said reject signal from said production line.

4. A system for optically inspecting high velocity individual flat sheets having scrolled and unscrolled edges in a production line for defects, each of said individual flat sheets being at spaced locations from each other and having a first dimension in the direction of movement and a second dimension perpendicular thereto, said system comprising:

a formed viewing window, said formed viewing window having a length perpendicular to said direction of movement and a width greater than said second dimension of each said individual flat sheet;

means receiving said individual flat sheets from said production line at said spaced locations for delivering each of said sheets over said formed viewing window at said high velocity, means for uniformly and continuously illuminating the surface of each said individual flat sheet along said length of said formed viewing window with high intensity diffused light as each said individual flat sheet is delivered over said formed viewing window by said delivering means, means receiving the reflected high intensity diffused light from the surface of each individual flat sheet for capturing a video image of each line across said length of each of said individual flat sheet independent of the velocity of each said individual flat sheet, each said line being one pixel wide and a sufficient number of pixels in length to equal said second dimension of each said individual flat sheet, means connected to said capturing means for storing an electronic image of each said individual flat sheet, said electronic image comprising a sufficient number of said captured lines to equal said first dimension of each said individual flat sheet, wherein said storing means is first capable of determining the edge of the first captured video line image and then is capable of storing all subsequent captured video line images adjusted to said determined edge so that any scrolled edge of said individual flat sheet is transformed into a straight edge in the corresponding electronic image thereby enabling the analysis of any defects present in said scrolled edge, means connected to said storing means for analyzing said stored electronic image of each said individual flat sheet for defects, said analyzing means issuing a reject signal when a defect is detected in said stored electronic image, and means receptive of said reject signal for removing the individual flat sheet corresponding to said reject signal from said production line.

5. A system for optically inspecting high velocity individual flat sheets having scrolled and unscrolled edges in a production line for defects, each of said individual flat sheets being at spaced locations from each other and having a first dimension in the direction of movement and a second dimension perpendicular thereto, said system comprising:

means for uniformly and continuously illuminating a portion of the surface of each said individual flat sheet along said second dimension with high intensity diffused light, means receiving the reflected high intensity diffused light from said portion of each individual flat sheet for capturing a video image of a line across said second dimension of said individual flat sheet, each said line being one pixel wide and a sufficient number of pixels in length to equal said second dimension of each said individual flat sheet, each pixel having a grey level value corresponding to the reflected high intensity diffused light from an area on said individual flat sheet, means connected to said capturing means for storing an electronic image of each said individual flat sheet, said electronic image comprising said sufficient number of pixels and a sufficient number of said captured lines to equal said first dimension of each said individual flat sheet, means for determining the transition edge of each captured video line image by issuing an edge signal, said storing means being capable of storing each captured video line image at the same starting address in response to said edge signal so that any edge configuration of said individual flat sheet is transformed into a straight edge in the corresponding electronic image thereby enabling the analysis of any defects present in said scrolled edge, and means connected to said storing means for analyzing the grey levels of pixels in said stored electronic image of each said individual flat sheet for defects, said analyzing means issuing a reject signal when a defect is detected in said stored electronic image.

6. The system of claim 5 further comprising means for delivering said sheets at said high velocities in a range up to 500 feet/minute.

7. The system of claim 5 wherein said illuminating means comprises:

a plurality of high intensity lights, a formed viewing window, said formed viewing window having length perpendicular to said direction of movement and a width greater than said second dimension of each individual flat sheet, means connected to said plurality of high intensity lights for uniformly directing light from said plurality of high intensity lights into said formed viewing window, and a diffuser placed a predetermined distance from said surface of each said individual flat sheet as each said individual flat sheet is delivered over said formed viewing window and connected to said directing means for uniformly diffusing said uniformly directed light onto said surface.

8. The system of claim 14 wherein said illuminating means further comprises means connected to said directing means for removing heat generated by said plurality of lights from said directing means so as to maintain the temperature of said directing means below a predetermined level.

9. The system of claim 5 wherein said illuminating means further comprises means for adjusting the intensity of said high intensity diffused light depending on the optical reflection of each said individual flat sheets.

10. The system of claim 5 wherein said line width corresponding to said pixel is at least 0.030 inch.

11. The system of claim 5 wherein said defect is greater than 0.070 inch in size.

12. The system of claim 6 further comprising:
means located on said delivering means for detecting the leading edge of each said individual flat sheet, said detecting means issuing an edge signal,
means connecting to said delivering means for generating a stream of encoder pulses corresponding to said velocity of each said individual flat sheet, and
means receptive of said edge signal and of said encoder pulses for activating said capturing means after each said individual flat sheet has traveled a present distance from said detecting means so that the first video line image captured corresponds to the first line on each said individual flat sheet.

13. The system of claim 12 wherein said detecting means comprises two sensors located near opposing sides of said second dimension of each said individual flat sheet.

14. The system of claim 5 wherein said capturing means is further capable of capturing said video images even if the delivered individual flat sheet has a skewness less than a predetermined acceptable value.

* * * * *